United States Patent [19]

Gordon et al.

[11] Patent Number: 5,223,486
[45] Date of Patent: Jun. 29, 1993

[54] INHIBITION OF CANCER PROCOAGULANT

[75] Inventors: Stuart G. Gordon, Denver, Colo.; Anna Falanga, Bergamo, Italy

[73] Assignee: University Research Corporation, Boulder, Colo.

[21] Appl. No.: 726,119

[22] Filed: Jun. 28, 1991

Related U.S. Application Data

[63] Continuation-in-part of Ser. No. 265,501, Nov. 1, 1988, abandoned.

[51] Int. Cl.$^5$ .............................................. A61K 37/02
[52] U.S. Cl. ..................................... 514/18; 514/19; 530/330; 530/331
[58] Field of Search .................... 514/18, 19; 530/330, 530/331

[56] References Cited

U.S. PATENT DOCUMENTS 4,461,833 7/1984 Gordon ............................ 435/183

OTHER PUBLICATIONS

Leytus et al. (1984) Proc. Natl. Acad. Sci. USA 81:3699-3702.
Gordon et al. (1985) Blood 66:1261-1265.
Falanga et al. (1989) Thrombosis Res. 54:389-398.

Primary Examiner—Ronald W. Griffin
Attorney, Agent, or Firm—Greenlee and Winner

[57] ABSTRACT

Peptidyl inhibitors, for example, peptidyl diazomethyl ketones and peptidyl methylsulfonium salts wherein the peptidyl moiety comprises two to ten amino acid residues inhibit cancer procoagulant, a cysteine proteinase, that is necessary for the viability of malignant cells. This invention provides for methods of cancer therapy and blood detoxification wherein these peptidyl inhibitors are used to destroy malignant cells.

15 Claims, 4 Drawing Sheets

(a) SEQ ID NO:1

Ser Val Ala Gln Ala Thr Ser Ser Ser Gly Glu Ala Pro Asp Ser Ile
1             5                   10                  15

Thr Trp Lys Pro Tyr Asp Ala Ala Asp Leu Asp Pro Thr Glu Asn Pro
            20                  25                  30

Phe Asp Leu Leu Asp Phe Asn Gln Thr Gln Pro Glu Arg Gly Asp Asn
            35                  40                  45

Asn Leu Thr Arg Ile Val Gly Gly Gln Glu Cys Lys Asp Gly Glu Cys
    50                  55                  60

Pro Trp Gln Ala Leu Leu Ile Asn Glu Glu Asn Glu Gly Phe Cys Gly
65                  70                  75                  80

Gly Thr Ile Leu Ser Glu Phe Tyr Ile Leu Thr Ala Ala His Cys Leu
                85                  90                  95

Tyr Gln Ala Lys Arg Phe Glu Gly Asp Arg Asn Thr Glu Gln Glu Glu
            100                 105                 110

(b) SEQ ID NO:2

Asp Ala Ala Asp Leu Asp Pro Glu Asn Pro Phe Asp Leu Leu
1             5                   10

(c) SEQ ID NO:3

Ser Ile Thr Trp Xaa Pro Xaa Ala
1             5

(d) SEQ ID NO:4

Glu Asn Pro Phe Asp Xaa Xaa Phe
1             5

Figure 4

INHIBITION OF CANCER PROCOAGULANT

CROSS REFERENCE TO RELATED APPLICATION

This application is a continuation-in-part of co-pending application Ser. No. 07/265,501, filed Nov. 1, 1988, now abandoned.

FIELD OF THE INVENTION

This invention relates to selective peptidyl inhibitors of cancer procoagulant (CP), a protein elaborated by malignant, but not normal, animal and human cells, and to the use of these selective peptidyl inhibitors in cancer therapy and in CP removal from blood.

BACKGROUND OF THE INVENTION

The suspected relationship between neoplastic disease and thromboembolic disorders, first recognized by Armand Trousseau in 1865, who described an increased incidence of venous thrombosis in a series of patients with gastric carcinoma, led to the identification of abnormal fibrin metabolism with malignant disease. An increased rate of fibrinogen turnover (Yoda et al. (1981) Thromb. Haemost. 46:706-709), an increase in plasma levels of fibrinogen/fibrin-related antigen (Merskey et al. (1980) Br. J. Haematol 44:655-670), and an increase in plasma levels of fibrinopeptide-A (a 16-amino acid peptide cleaved from the A chain of fibrinogen by thrombin) have been observed in virtually all patients with acute leukemia and solid tumors (Yoda et al. (1981) supra). It is believed that subclinical activation of blood coagulation may be a reflection of the interdependence of tumor growth and fibrin generation (Rickles et al. (1983) Blood 62:14-31). Fibrin was found deposited on the advancing margin of solid tumors and also on blood-borne, potentially metastatic, malignant cells. Administration of anticoagulants and fibrinolysins decreased tumor growth and metastasis (Wood et al. (1955) in The Pathogenesis of Cancer, J. E. Gregory (ed.), Fremont Foundation, Pasadena, Calif., pp. 140-151). Thus, it appeared clear that altered fibrin metabolism was associated with malignant tissue, but it was not clear what caused the altered activity of the coagulation cascade that resulted in abnormal fibrin deposition.

To explain the hypercoagulable state associated with neoplasia, the concept emerged that malignant tissue produced a substance capable of initiating coagulation. Among the mechanisms that can promote abnormal activation of blood clotting in malignancy, tumor-associated procoagulants are considered to play a prominent role. In 1975 Gordon et al. (Thromb. Res. 6:127-137) reported the isolation of a protein called cancer procoagulant (CP) from rabbit V2 carcinoma cells that initiated coagulation by a mechanism that was distinguishable from that of the intrinsic and extrinsic pathways. CP was shown to be different from tissue factor, which is normally released from damaged cells and participates via the extrinsic pathway in the activation of the coagulation system. It was shown that CP initiated coagulation in the absence of factor VII and was inhibited by diisopropylfluorophosphate (DFP), two characteristics that distinguish CP from tissue factor. CP has now been characterized as a cysteine proteinase having a molecular weight of 68,000 and capable of initiating coagulation by directly activating factor X in the coagulation cascade (Gordon, U.S. Pat. No. 4,461,833; Falanga et al. (1985) Biochem. 24:5558-5567, and Biochim. Biophys. Acta 831:161-165). Most importantly, although CP could be extracted from tumor cells, no CP activity or antigen could be detected in extracts from normal cells or from benign melanocytic lesions (Donati et al. (1986) Cancer Res. 46:6471-6474; Falanga et al. (1988) Blood 71:870-875). The presence of CP was clearly associated with the malignant phenotype and its activity appears to be particularly high in metastatic cells.

For years investigators had sought to identify diagnostic markers of cancerous cells for the purpose of developing cancer therapies. In 1970, Bubenek et al. (Int. J. Cancer 5:310), demonstrated that serum from cancer patients contained antibodies that bound to tumor cell surface antigens Subsequently, many reports were published on the presence of antigens on the surface of human melanoma and on other neoplastic cells. The ultimate goal in these investigations was to utilize the corresponding specific antibodies in the immunotherapy of cancer.

Of the many antigens characterizing tumor cells, some of the more notable are carcinoembryonic antigen (CEA), alpha-fetoprotein (AFP) and acute lymphoblastic leukemia associated antigen (cALLA) A number of other tumor-associated antigens have been studied as possible tumor detectors (Hellstrom et al. (1982) Springer Semin. Immunopathol. 5:127). In most cases there is little evidence to indicate that any of these antigens have value as a potential tumor marker.

Investigation was also undertaken to test different drug therapies for their effectiveness in fighting neoplasia. In 1976 the hypothesis was tested in man that anticoagulant drugs could modify favorably the course of human cancer. Warfarin, an agent shown to be effective in a variety of animal tumor models, was found to be therapeutically associated with (i) a significant prolongation in the time to first evidence disease progression and, (ii) a significant improvement in survival for patients with small cell carcinoma of the lung (Zacharski et al. (1984) Cancer 53:2046). In 1981, the antiplatelet drug RA-233 (mopidamol) was tested for treatment of human malignancy. RA-233 is a phosphodiesterase inhibitor that has been shown to limit progression of tumors in experimental animal models (Zacharski et al. (1982) Am. J. Clin. Oncol. 5:593). In this study, RA-233 was associated with a statistically significant prolongation of survival in patients with nonsmall cell lung cancer limited to one hemithorax (Zacharski et al. (1987) Thromb. Haemost. (Suppl) 58:508). None of the other tumor types was found to respond to treatment with RA-233. Although it is possible that both of these drugs, warfarin and RA-233, may act outside the role of anticoagulant/platelet agent, this approach was considered to have merit and is under further examination for continuation.

It is still believed today that the finding of a selective marker diagnostic of tumorigenic cells would enable detection of malignant cells and would then allow treatment of neoplasia. Such a diagnostic marker was shown to be CP, first isolated from rabbit V$_2$ carcinoma (Gordon et al. (1975) Thromb. Res. 6:127-137; (1981) J. Clin. Invest. 67:1665-1671). CP, a cysteine proteinase, was subsequently found in tissue extracts of the following human cancers: breast, colon, vagina, kidney, lung, blood and bone marrow (Gordon et al. (1975) supra; (1979) J. Natl. cancer Inst. 62:773-776; Falanga et al. (1988) Blood 71:870-875). CP has also been described in transformed hamster fibroblasts (Gordon et (1978) Cancer Res. 38:2467-2472), mouse Lewis lung carcinoma (3LL) cells (Colucci et al. (1980) Thromb. Res. 18:589-595), B16 mouse melanoma cells (Donati et al. (1986) Cancer Res. 46:6471), mouse Ehrlich ascites carcinoma cells (Curatolo et al. (1979) Br. J. Cancer 40:228-233), and mouse JW sarcoma cells (Curatolo et al. (1979) supra). However, in none of these studies was CP found in extracts of adjacent normal tissue. Thus, CP appeared to be a diagnostic marker associated exclusively with the malignant state.

Cysteine proteinases constitute a major class of proteolytic enzymes characterized by an active sulfhydryl group that participates in catalysis by means of acylthioester formation (Fink et al. (1976) Biochemistry 15:5287-5293). Proteinases of this class have been shown to function in protein turnover (Dayton et al. (1976) Biochemistry 15:2150-2158), hormone metabolism (Rupnow et al. (1979) Biochemistry 18:1206-1212) and viral protein processing (Korant et al. (1979) Proc. Natl. Acad. Sci. 76 2992-2995). In order to be able to eventually study the in vivo activities of individual cysteine proteinases, selective inhibitors for enzymes of this class have been prepared and examined first in in vitro studies.

Compounds having the reactive group, diazomethyl ketone, were the first to be examined as potential reagents selective for cysteine proteinases. Carbobenzyloxyphenylalanyl diazomethyl ketone (Z-Phe diazomethyl ketone) and carbobenzyloxy-phenylalanylphenylalanyl diazomethyl ketone (Z-Phe-Phe diazomethyl ketone) were found to be irreversible inhibitors of papain, a model cysteine proteinase from papaya (Leary et al. (1977) Biochemistry 16:5857-5861). The dipeptide derivative was about 200-fold more effective an inhibitor than Z-Phe diazomethyl ketone. Moreover, more importantly, these diazomethyl ketones were found to be without effect on serine proteinases (Leary et al. (1977) supra), metalloproteinases and their effect on aspartate proteinases requires copper ions (Shaw et al. (1980) Biochem. J. 186:385-390). Because of this relative chemical inertness, peptide diazomethyl ketones were deemed to be useful for the study of the role of sulfhydryl proteinases in normal and pathological processes.

Both Z-Phe diazomethyl ketone and Z-Phe-Phe diazomethyl ketone were shown to also inhibit cathepsin B. The dipeptide derivative was three orders of magnitude more effective, indicating the importance of occupation of an additional binding site (Leary et al. (1977) Biochem. Biophys. Res. Comm. 79:926-931). Cathepsin B, a lysosomal cysteine proteinase present in many animal tissues, plays a regulatory role in protein turnover. In addition, cathepsin B has been shown (Burleigh et al. (1974) Biochem. J. 137:387-398) to possess collagenolytic activity, which may be responsible for initial stages of extracellular breakdown of connective tissue (Holtzman (1975) Lysosomes: A Survery, Springer-Verlag, New York, pp. 110-115 and 179-184). Again, the availability of enzyme inhibitors selective for only cysteine proteinases would permit exploration of the potential role of cysteine proteinases, e.g., cathepsin, in metastasis and in other metabolic processes.

A third inhibitor of this class, Z-Phe-Ala diazomethyl ketone, was shown to be a powerful inactivator of bovine spleen cathepsin B with $K_i = 1.7-10^{-6}M$ (Watanabe et al. (1979) Biochem. Biophys. Res. Comm. 89:1354-1360). The idea that the rate of reaction of a cysteine proteinase with various inhibitors depended on the specificity of the enzyme was tested on cathepsin B and L, both cysteine proteinases of lysosomal origin. The role of cathepsin L is probably not limited to lysosomal protein degradation since precursor forms are secreted by fibroblasts upon transformation and by stimulated inflammatory macrophages (Kirschke et al. (1988) FEBS Lett. 228:128-130). Under assay conditions comprising a very sensitive substrate, Z-Phe-Arg-4-methyl-7-coumarylamide, Z-Phe-Ala dimethyl ketone exhibited an affinity for cathepsin L which was about 2000-fold higher than for cathepsin B from rat and human. Z-Phe-Phe diazomethyl ketone, on the other hand, selectively inactivated cathepsin L in a certain concentration range, whereas it reacted reversibly with cathepsin B from several species (Kirsche et al. (1981) Biochem. Biophys. Res. Comm. 101:454-458).

In 1981 Green and Shaw (J. Biol. Chem. 256:1923-1928) undertook a comprehensive examination of a number of different diazomethyl ketones and compared their rates of inactivation of the endopeptidases clostripain, an enzyme of trypsin-like specificity, streptococcal proteinase and cathepsin B and an exopeptidase, cathepsin C. A number of interesting features emerged: (i) Z-Phe-Ala diazomethyl ketone, one of the most effective inactivators of cathepsin B and L, was absolutely inert toward clostripain, illustrating the type of selectivity attainable by this approach; (ii) the charged amino acid derivative, Z-Lys diazomethyl ketone, proved to be a powerful inhibitor of cathepsin B; (iii) cathepsin B and the streptococcal proteinase were particularly sensitive to reagents having phenylalanine in the penultimate, or $P_2$, position, rather than in $P_1$; (iv) for cathepsin B, variation in $P_1$ in the series Z-Gly-Gly-Y diazomethyl ketone does not yield an effective inhibitor, reinforcing the belief that phenylalanine in $P_2$ contributes greatly to binding. In later studies, Kirschke et al. (1988) FEBS Lett. 228:128-130 found that in contrast to cathepsin B the $P_1$ region of cathepsin L has the ability to accommodate large hydrophobic side chains, and they showed that Z-Phe-Tyr(O-t-Bu) diazomethyl ketone inactivated cathepsin L with a rate $2.5 \times 10^4$ greater than that for cathepsin B.

Overall, these results demonstrated that the effectiveness of the inhibitors correlated with the specificities of the individual enzymes. Furthermore, it was shown that peptidyl diazomethyl ketones are unreactive with thiols, such as mercaptoethanol, mercaptoethylamine and glutathione, and with nonproteinase enzymes having an active center thiol. This property and the lack of reactivity toward other classes of proteinases suggest the usefulness of this class of peptidyl inhibitors as diagnostic reagents for both in vitro and in vivo studies (Green et al. (1981) supra).

A different group of peptide derivatives containing a sulfonium salt was found by Shaw (1988) J. Biol. Chem. 263;2768-2772, to act as affinity-labelling reagents of cysteine proteinases. Peptides containing hydrophobic side chains, e.g., Z-He-Ala-CH$_2$S$^+$(CH$_3$)$_2$ showed considerable effectiveness for the inactivation of papain and cathepsin. Sulfonium salts having the general structure Z-Lys-CH$_2$S$^+$-(alkyl)$_2$ irreversibly inactivated the cysteine proteinase clostripain, but also appeared to inhibit two serine proteinases, although with complex kinetic responses. The affinity of the peptidyl sulfonium salts tested was in the nanomolar range for clostripain, whereas for those serine proteinases showing an effect, the affinities were approximately 10 $\mu$M (Rauber et al. (1988) Biochem. J. 250:871-876). It is believed that peptidyl methylsulfonium salts are effective as cysteine proteinase inhibitors and that they can be used to study selected enzymes.

The discovery that certain peptidyl diazomethyl ketones and peptidyl sulfonium salts were selective in vitro inhibitors of cysteine proteinases raised the possibility that these inhibitor compounds would be used in vivo to probe the role of different cysteine proteinases in various metabolic processes. Thus, the overall effect of these reagents on protein metabolism was tested in isolated rat hepatocytes. Z-Phe-Phe diazomethyl ketone and Z-Phe-Ala diazomethyl ketone were found (Grinde (1983) Biochim. Biophys. Acta 7575:15–20)to reduce lysosomal protein degradation and synthesis. At a concentration of $10^{-4}$ M, both diazomethyl ketones caused between 55 and 70% inhibition of protein degradation and between 45 and 65% inhibition of protein synthesis. At lower concentrations, e.g., $10^{-5}$M, Z-Phe-Al a diazomethyl ketone inhibited protein synthesis by 21% whereas Z-Phe-Phe diazomethyl ketone showed 16% inhibition. The substantial suppression of protein metabolism by these two peptidyl diazomethyl ketones indicates that particular caution will have to be exercised in monitoring possible side reactions associated with the utilization of these inhibitory reagents in in vivo or on cellular systems.

Since CP, a cysteine proteinase, appears to be a diagnostic marker of neoplasia, the identification of compounds that act as inhibitors of CP would permit detailed investigation of the role played by CP in malignancy and also of the association between thromboembolic disorders and neoplastic disease. To date, chemical compounds that show specific inactivation of CP have not been reported.

SUMMARY OF THE INVENTION

This invention provides for a method of inhibiting cancer procoagulant which provides for a method of cancer therapy wherein patients diagnosed as having a tumor are administered therapeutically effective amounts of chemical compounds that are peptidyl inhibitors. These peptidyl compounds are selective inhibitors of CP. It has been shown previously in a copending application (U.S. patent application Ser. No. 247,843, filed Sep. 22, 1988), incorporated herein by reference, that anti-CP antibodies cause the lysis of malignant cells and that CP is required for the survival of malignant cells. Hence, the presence of compounds such as peptidyl inhibitors, that selectively inactivate CP, retards or prevents the formation of different types cf tumors, reduces existing tumors, decreases tumor metastasis and inactivates malignant cells in a treated patient that includes, but is not limited to, humans, primates, mice, rats, rabbits, dogs, horses, cows and sheep.

Tumor prevention is effective with peptidyl inhibitors that have a peptidyl moiety that comprises between two and ten amino acid residues, each of which is either chemically unaltered or viably modified or substituted, i.e., conjugated to different protecting groups or other desired chemical ligands. Viably modified or substituted peptidyl inhibitors are considered to be equivalent to inhibitors in which amino acids are unmodified whenever such modifications do not prevent detection of inhibitory activity in the final product and do not prevent the final product from being therapeutically effective. Methods to assess the effectiveness of given dosages of peptidyl inhibitors are described in the instant application, e.g., inhibition of factor X activation, inhibition of the protein C system and degradation of protein S, and encompass standard techniques which can be easily employed by those of ordinary skill in the art. In a preferred embodiment of this invention, peptidyl diazomethyl ketones and peptidyl sulfonium salts are designed to have a desired substrate specificity. The choice of amino acid residue and the arrangement or sequence of amino acids within the peptidyl moiety confers a level of affinity between the inhibitor and its target enzyme. Desired peptidyl inhibitors are chemically synthesized and purified. Preferably, the choice of inhibitors and the level of purity are such that at concentrations of inhibitor administered, undesired side reactions are not produced. Such side reactions are readily detected and dosages adjusted by those of ordinary skill in the art. Tumor therapy is considered to be effective when it can be shown that tumor size has been reduced, or that tumor metastasis decreased, or that malignant cells are destroyed.

This invention elucidates peptidyl derivatives which function as specific inhibitors of CP. These compounds are used in this invention as affinity ligands believed to bind to the active site of CP, a cysteine proteinase. Two different classes of peptidyl derivatives, peptidyl diazomethyl ketones and peptidyl sulfonium salts, are exemplified in this invention and methods for the synthesis of representative dipeptidyl diazomethyl ketones, tripeptidyl diazomethyl ketones and dipeptidyl sulfonium salts are described. These representative structures may be chemically and viably modified, extended or truncated by those of ordinary skill in the art using standard methods such that the final product still shows inhibition of CP. In this invention peptidyl derivatives are described by amino acid sequence, using standard three letter abbreviations known in the art. All amino acids described herein are L-amino acids unless otherwise specified.

For tumor therapy, peptidyl inhibitors of CP may be delivered by parenteral infusion or other means known to the art in patients having diagnosed tumors. Peptidyl inhibitors may also be injected directly into prelocalized tumors. Alternatively, therapeutically effective amounts of peptidyl inhibitors may be administered ex vivo to a patient. For example, ex vivo passage of fluid (e.g., blood) from a patient may be shunted through a medium containing a therapeutically effective concentration of peptidyl inhibitor before being returned to the patient. Tumor therapy using peptidyl inhibitors of CP can also be used adjunctly to other types of cancer therapy, for example, in conjunction with radiation therapy or chemotherapy. Also, it can be used in patients having a diagnosed tumor as a preventive measure against tumor metastasis in conjunction with surgery for tumor or non-tumor conditions when the probability for increased incidence of tumor metastasis is enhanced.

This invention also contemplates the use of peptidyl inhibitors of CP in cancer patients as anti-thrombotic agents. CP not only acts directly to initiate coagulation, it also acts to prevent the normal suspension of coagulation usually regulated by the protein C system. Thus, according to this invention, the abnormally high level of coagulation observed to be associated with neoplasia can be reduced by treatment with peptidyl inhibitors of CP.

This invention also provides a method for CP removal from blood using peptidyl inhibitors to bind and inactivate CP, which is a necessary component for the viability of malignant cells. Freshly drawn or stored blood, for example, blood to be used for transfusion into a patient, is treated in vitro with an effective concentration of peptidyl inhibitor. Excess inhibitor molecules are removed subsequently from the treated blood by filtration or dialysis or other methods known to the art. The resultant detoxified blood is rendered virtually devoid of the presence of active, unbound CP, and of malignant, possibly metastatic, cells.

Additionally, this invention provides a method for compromising malignant cells. The binding of peptidyl inhibitors to CP, e.g., peptidyl diazomethyl ketones or peptidyl sulfonium salts renders malignant cells ineffectual within body fluids or tissues or on established tumors. Thus, in cancer patients the cytotoxic property of CP inhibitors weakens or kills in situ malignant cells and also those which may be in the migratory or invasive phase of metastasis. Therefore, cancer therapy with peptidyl diazomethyl ketones or peptidyl sulfonium salts inhibitory to CP provides a method for inactivating or destroying malignant cells and, thus, for preventing the establishment of secondary tumors.

DETAILED DESCRIPTION OF THE INVENTION

The following definitions are provided in order to remove ambiguities to the intent or scope of their usage in the specification and claims.

Cancer procoagulant (CP) is a proteolytic enzyme that functions directly in coagulation, by activating factor X. It also acts to prevent the normal suspension of coagulation normally regulated by the protein C system. CP is a 68 kD protein having an isoelectric point of 4.8. Although several properties of CP make it unique among coagulation proteinases, the most notable characteristic is its cysteine proteinase activity; it is sensitive to cysteine proteinase inhibitors, such as iodoacetamide and mercury. CP has been found only in neoplastic, fetal and amnion-chorion cells; it has not been found in normally differentiated tissue. Thus, CP is thought to be an antigenic marker for malignancy. The presence of CP can be detected enzymatically using a one-stage plasma recalcification assay.

Peptidyl inhibitors are small peptides coupled at the carboxyl terminus to either a diazomethyl or a methylsulfonium group. The peptidyl moiety comprises from two to ten amino acid residues. The amino acid residues may be chemically truncated, extended, substituted or otherwise modified, e.g., by addition of protecting groups or other desired ligands, providing that the final product still exemplifies inhibitory activity. Such peptidyl inhibitors may be synthesized by persons of ordinary skill in the art using conventional chemistry, as described in Example 1. The inhibitory activity of peptidyl inhibitors can be monitored as described in Examples 3 and 4 and the effectiveness of substituted or modified peptidyl inhibitors can be assessed using these methods in addition to others well-known by those of ordinary skill in the art.

The term viably modified, as used herein, refers to the chemical modification of compounds which are peptidyl inhibitors of CP in such a way that a modified peptidyl inhibitor is deemed to be equivalent to an unmodified peptidyl inhibitor, i.e., that it still exhibits binding to CP and causes inhibition of coagulation, as assessed by methods described in the instant application, e.g., inhibition of factor X activation and inhibition of the protein C system and degradation of protein S, as well as by alternate methods known to those of ordinary skill in the art. Such viable modification comprises the addition or deletion of groups such as alkyl, phenyl, benzyl, carbobenzyloxy, t-butoxycarbonyl, tosyl, 7-amino-4-methylcoumaryl or other protecting groups or desired ligands, or the substitution addition or subtraction of amino acids or peptides.

The term therapeutically effective as used herein is defined by the situation wherein tumor formation is retarded or prevented, tumor metastasis is decreased, tumor size is reduced or malignant cells are destroyed. As indicated herein, peptidyl inhibitors to CP cause the destruction of cancer cells. The desired degree of therapeutic effectiveness to be achieved by in vivo administration of peptidyl inhibitors depends on numerous factors known to the art, such as tolerance of the patient to the dosage, presence or absence of known metastatic cells, tumor size and location, etc. Dosages of peptidyl inhibitors having the desired degree of effectiveness are determined by art-known methods. Similarly, peptidyl inhibitor dosages for ex vivo and in vitro cancer therapy can be ascertained readily by persons of ordinary skill in the art using routine biochemical inhibitor assays.

The term compromising malignant cells, as used herein, refers to any inactivation, weakening, inhibition, slowing, destruction, lysis or killing of target cells upon exposure to peptidyl inhibitors. That a cell has been compromised can be verified using morphological observations, histochemistry and the monitoring of other whole cell parameters, such as cell growth and active transport.

Relative inhibitory activity is a term used herein to compare the inhibitory effect of a peptidyl inhibitor on different enzymes. It is preferred that measurements of inhibitory activity be carried out under essentially standard assay conditions in order to clearly assess, through comparison of $K_i$ values and other indices of specific inhibition, the degree of specificity of a given inhibitor for a particular enzyme. At other times, inhibitors may be compared directly in a given assay as is known and routinely carried out in the art and their inhibitory effects may be reported in terms that show an immediate relativity among the compounds tested.

Selective, as used herein, implies specificity and enhanced affinity of a peptidyl inhibitor toward cancer procoagulant, i.e., a very specific inhibitor of cancer procoagulant with minimal action on other cysteine proteinases, in particular, on cysteine proteinases critical for maintaining normal metabolic and physiologic functions.

Amino acid refers to any L-amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

The initial discovery by the applicant of a protein diagnostic of neoplastic cells now provides the opportunity to create from that discovery an invention which, in the present case, provides for a method to detect cancerous cells, to treat and to destroy malignant cells and to prevent metastasis. This invention embodies a method of cancer therapy which takes advantage of the discovery that neoplastic cells produce a protein, CP, that is not synthesized by normal cells. The instant invention utilizes this information to design a treatment of cancer which affects specifically cancer cells and not healthy normal cells. This ability to treat specifically neoplastic cells gives the method of this invention considerable advantage over many cancer treatment regimens being used today. The preferred method of cancer therapy described in this invention utilizes peptidyl diazomethyl ketone and peptidyl sulfonium salt inhibitors as specific agents to treat cancer and prevent metastasis. When such peptidyl inhibitors are exposed to either normal or malignant cells, they react only with a component of malignant cells. Thus, these peptidyl inhibitors are able to target malignant cells and to distinguish between normal and malignant cells.

The instant invention exemplifies two classes of peptidyl inhibitors, the diazomethyl ketones and the methylsulfonium salts, that are effective in cancer therapy. Their effectiveness is based on the fact that these peptidyl inhibitors bind irreversibly and with high affinity to CP, a cysteine proteinase, and in this way inhibit the enzymatic activity associated with CP. Many of these peptidyl inhibitors will bind to other cysteine proteinases, but in the specific embodiment of this invention, the preferred peptidyl inhibitors show an approximately >100-fold higher relative inhibitory activity to CP than to non-CP cysteine proteinases.

In both the peptidyl diazomethyl ketones and the peptidyl sulfonium salts, the peptidyl sequence determines the effectiveness of the affinity-labelling portion of the inhibitor molecule in inactivating cysteine proteinases. For an ideal application of this approach to the inactivation of CP, one would need to know the sites of factor X, thrombomodulin and protein S at which CP acts and utilize these sequences as guides in designing inhibitory compounds. However, this information is not currently available. Meanwhile, this invention presents a selection of peptide derivatives that inhibit cysteine proteinases and bind preferentially to CP.

The peptidyl inhibitors described in the present invention have the general structure wherein Z is H, carbobenzyloxy or other commonly used protecting group, e.g., t-butoxy carbonyl, tosyl, benzyl, 7-amino-4-methylcoumaryl, etc., R is an amino acid side chain or a modified or derivatized amino acid side chain selected independently from the group consisting of L-amino acids such that the final peptidyl moiety comprises amino acid residues that are the same or different from each other, n is 2-10, and Y is OH, a diazomethyl ($-CH_2-N=N^+$) or a methylsulfonium group, where $X_1$ and $X_2$ are alkyl, phenyl or benzyl groups. These compounds are chemically synthesized using routine chemical procedures, as described in Example 1. The peptidyl moiety comprises from two to ten amino acid residues and the carboxyl terminus is unaltered or coupled to a diazomethyl ketone or a methylsulfonium group. Compounds wherein Z is H and Y is OH describe peptides. Depending on the amino acid sequence, such peptides may be designed to be very specific and to bind with high affinity. In synthesizing such peptides, the amino acid sequence is active-site directed in order to maximize the selectivity of the synthetic peptide. Compounds of this sort, having an unmodified amino acid sequence, resemble cystatins, which are naturally-occurring peptides that are reversible inhibitors of cysteine proteinases. It is further contemplated in this invention that the amino acid residues may be chemically modified or derivatized, on condition that the final product still exhibits inhibitory activity. A modified or derivatized amino acid is one wherein functional side groups or end groups are protected by reaction with a ligand to form an adduct or compound therewith, e.g., amides, esters, t-butoxy carbonyls, carbobenzyloxys, tosyls, benzyls, 7-amino-4-methylcoumaryls and the like, as is well-known in the art. The inhibitory activities and specificities of peptidyl inhibitors can be monitored as described in Examples 3 and 4.

In a specific embodiment of this invention the representative peptidyl diazomethyl ketone and peptidyl sulfonium salt inhibitors were shown (see FIG. 1) to be without inhibitory effect on control blood procoagulants (tissue factor (TF) and Russell's viper venom (RVV)) which are known to function via serine proteinase activity. However, these peptidyl inhibitors did inhibit the control cysteine proteinase, papain.

The inhibitory effect of different peptidyl inhibitors on papain was compared with that for CP. As described by FIG. 2, there was a differential inhibition of papain and CP by each of the peptidyl diazomethyl ketones. While Z-Phe-Ala diazomethyl ketone (D1) and Z-Pro-Gly-diazomethyl ketone (D3) each blocked activity of both CP and papain to a similar extent, Z-Phe-Gly diazomethyl ketone (D2), Z-Gly-Gly-Val diazomethyl ketone (D4), Z-Ala-Ala-Pro diazomethyl ketone (D5) and Z-Ala-Ala diazomethyl ketone (D6) were all more effective inhibitors of CP than of papain. D1 (Z-Phe-Ala diazomethyl ketone) and D2 (Z-Phe-Gly diazomethyl ketone) have a phenylalanine residue in the P2 position and either an alanine or glycine reside in the P1 position. The presence of glycine in the P1 position improved the inhibition of CP but had little effect on papain inhibition. However, the presence of proline in the P2 position significantly reduced the inhibitory capacity of D3 (Z-Pro-Gly diazomethyl ketone) compared to D2 (Z-Phe-Gly diazomethyl ketone) for both papain and CP. Both CP and papain appeared to have a higher affinity for phenylalanine than for proline. There was no difference between the inhibition of CP and papain by D3.

Figure 2:
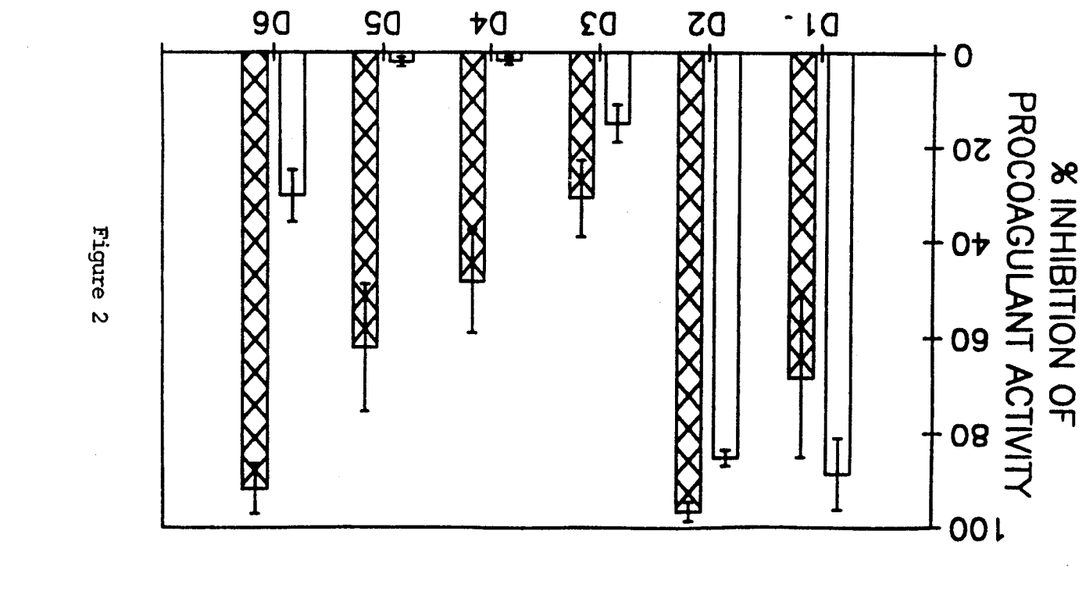
FIG. 2 documents the inhibition of papain (☐) and cancer procoagulant (CP) (■) by 100 μM peptidyl diazomethyl ketones. Samples were incubated with the six peptidyl diazomethyl ketone reagents and assayed for their procoagulant activity in normal plasma. The percent inhibition was calculated as the percent increase in clotting time from the uninhibited sample.

Both D4 (Z-Gly-Gly-Val diazomethyl ketone) and D5 (Z-Ala-Ala-Pro diazomethyl ketone) were poor inhibitors of papain and significantly better inhibitors of CP. The small, nonpolar amino acids in D4 appear to have a higher affinity for CP than papain. The presence of proline in the P1 position of D5 appears to impair the inhibitory capacity of D4 toward CP less than when proline is in the P2 position, as in D3.

While D6 (Z-Ala-Ala diazomethyl ketone) is a moderately poor inhibitor of papain, it is a good inhibitor of CP. Elimination of proline from the P1 position improved its affinity for both papain and CP. The presence of phenylalanine in the P2 position improves the inhibitory capacity of a diazomethyl ketone for papain; CP inhibition is improved with an alanine in the P2 position.

Figure 3:
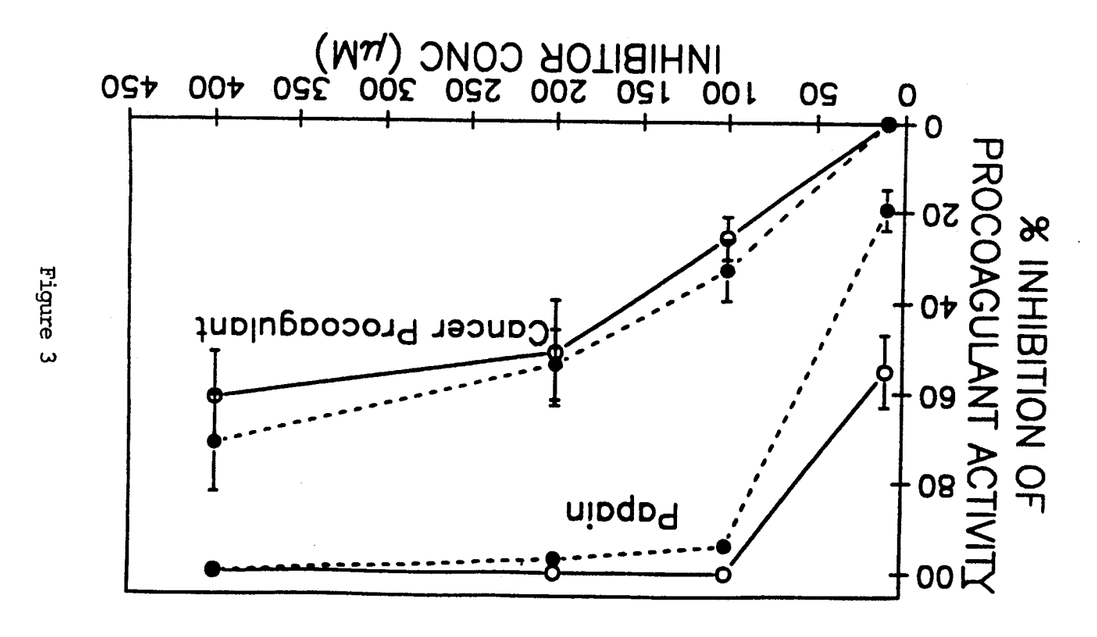
FIG. 3 illustrates the inhibition of papain (☐) and cancer procoagulant (CP) (■) by peptidyl sulfonium salts. Papain and CP were incubated with various concentrations of either Z-Phe-Ala-$CH_2S^+(CH_3)_2$ (S1) (—) or Z-Phe-Lys-$CH_2S^+(CH_3)_2$ (S2) (---) and assayed for procoagulant activity. The percent inhibition was calculated as the percent increase in clotting time from the uninhibited sample.

Studies with peptidyl sulfonium salts also give indications of differences in the substrate binding regions of papain and CP as illustrated in FIG. 3. The two peptidyl sulfonium salts evaluated in this study were moderately poor inhibitors of CP. S1 (Z-Phe-Ala sulfonium bromide) inhibited CP 26% while the same concentration (100 μM) of D1, with the same peptide, inhibited CP 68%, almost 3 times greater. Substituting the polar, basic amino acid, lysine, for alanine in S2 (Z-Phe-Lys sulfonium bromide) had little effect on the inhibition of CP and seemed to reduce the inhibition of papain.

The results of the inhibitor studies encompassed within this invention extend toward the goal of obtaining a very specific inhibitor of CP, that is, one with minimal action on other cysteine proteinases. In a specific embodiment, the present invention provides peptidyl inhibitors that act on cysteine proteinases, yet give differential effects on papain and CP, providing evidence that the active centers of papain and CP are not the same. Thus, this invention provides model peptidyl inhibitors for the design of yet more powerful and selective inactivators of CP. Such CP specific peptidyl inhibitors can be designed by different approaches, for example, by empirical probing of the active center of CP, or by defining the cleavage site in factor X, thrombomodulin and protein S produced upon activation by CP, followed by synthesis of a peptidyl diazomethyl ketone or peptidyl sulfonium salt incorporating this sequence information. In addition to the natural recognition sequence that promotes binding of CP, some amino acid substitutions may be made to take advantage of possible topographical features of the active center of CP to increase inhibitory affinity and promote discrimination from other cysteine proteinases.

During the course of studies to purify and characterize CP, Applicants demonstrated that CP directly activated factor X. However, it was noted that the protein stained pattern on SDS-PAGE was slightly different than the RVV activation of factor X control. In addition, the chromogenic assay for CP activated factor X showed very poor sensitivity and, generally, did not work well. In studies of inhibition by peptidyl diazomethyl ketones, the inhibitors that seemed to be most effective were very different than those that effectively blocked the activity of that papain control. Taken together, these data suggest that Cp may have a different active site configuration and/or a different amino acid recognition sequence in the substrate proteins it hydrolyzes. Therefore, in a specific embodiment of the present invention, the site of cleavage of human X by CP was determined. The primary cleavage sequence is set forth in the sequence listing as SEQ ID NO:2. Two other secondary cleavage sites are set forth in the sequence listing as SEQ ID NO:3 and SEQ ID NO:4. Cysteine proteinases are believed to key off the P2 amino acid on the carboxyl side of the hydrolyzed bond. The data presented in FIG. 4 indicate that the primary cleavage site of Factor X is governed by proline $-20$ (SEQ ID NO:1) and the secondary sites are governed by proline $-13$ and $-28$ (SEQ ID NO:1). These results are in contrast to the controlling amino acid, i.e., arginine-52 (SEQ ID NO:1), that governs the cleavage site of Factor X by normal serine proteinase activation. These data in FIG. 4 confirm the direct activation of Factor X by CP and suggest that CP may be a new class of cysteine proteinase.

It is believed in the present invention that within each class of inhibitors, the peptidyl compounds that were tested are representative of other peptidyl structures which have equivalent functionality, i.e., bind to CP and inhibit coagulation in a plasma recalcification clotting time assay. In other words, a viably modified peptidyl inhibitor is deemed to be equivalent to an unmodified peptidyl inhibitor whenever the structure that is chemically modified, for example, by adding or deleting ligands or by substituting, adding or subtracting amino acids or peptides, still exhibits binding to CP and causes inhibition of coagulation, as assessed by methods described in the instant application (i.e., inhibition of factor X activation, inhibition of the protein C system or degradation of protein S), as well as other methods that are known to those of ordinary skill in the art.

The utilization of peptidyl inhibitors of both the diazomethyl ketone and the sulfonium salt classes to compromise cancer cells is contemplated in the instant invention. This results from the observation that these peptidyl inhibitors bind to CP, a component of malignant cells which has been shown (Gordon, U.S. patent application Ser. No. 247,843) to be necessary for the survival of malignant cells. It is contemplated that the binding of peptidyl inhibitors to CP facilitates the destruction of malignant cells, for example, by potentiating susceptibility to a chemotherapeutic agent of choice. It is a specific embodiment of this invention that the binding of peptidyl inhibitors to CP of malignant cells results in the inactivation, slowing or weakening of malignant cells, rendering them less potent or less viable. In a more preferred embodiment, the binding of peptidyl inhibitors causes cell lysis, resulting in the destruction and killing of malignant cells. Thus, the binding of peptidyl inhibitors to CP essentially removes free or active CP and interferes with the functioning of CP as a component necessary for the viability of malignant cells. More important is the fact that an agent that is capable of destroying malignant cells is potentially capable of preventing the establishment of secondary tumors and, thus, of preventing tumor metastasis.

An additional role for inhibitors of CP is brought to light in this invention. Under normal conditions in the absence of malignant cells comprising CP, the coagulation cycle is internally regulated by the protein C system, which is responsible for the cyclical shutting down of coagulation through inactivation of fibrinogen proteolysis to produce fibrin. Hence, the system of coagulation factors responsible for initiation of coagulation is counterbalanced with a system of specialized factors that function to decrease fibrin deposition and bring the coagulation cycle to virtual completion. In the presence of CP, the protein C system is inactivated, resulting in a continued production of fibrin and, consequently, unchecked coagulation. CP binds to thrombomodulin, resulting in the inactivation of protein S; inactivation of protein S prevents degradation of key coagulation factors, e.g., factor V and factor VII, an enzymatic step responsible for suspension of the coagulation cycle, and thereby, coagulation continues unchecked. Such an induced state of thrombosis is inactivated by peptidyl inhibitors of CP. Since thrombotic disorders are often associated with neoplastic disease, this invention exemplifies a critical role for peptidyl inhibitors, e.g., peptidyl diazomethyl ketones and peptidyl sulfonium salts as antithrombotic agents in cancer patients.

Further, in this invention, peptidyl inhibitors specific to CP are used to target and destroy invasive or in situ malignant cells in body tissues and fluids. In a specific embodiment of this invention, a method is provided for parenterally injecting a patient having a diagnosed tumor with an appropriate solution of peptidyl inhibitor. Such tumor treatment with peptidyl inhibitor can constitute a primary therapy or an adjunct therapy in addition to, for example, chemical or radiation therapy. Cancer therapy with peptidyl inhibitors can also be used as a preventive measure against tumor metastasis in cancer patients, and even in patients not previously diagnosed as having tumors, in conjunction with, (i.e., before or during) surgery, when the incidence of tumor perturbation leading to malignant cell shedding and metastasis can occur with increased probability.

In a more preferred embodiment of this invention, peptidyl inhibitors can be delivered to a patient through intravenous injection or injection directly into the tumor site, prelocalized using established medical diagnostic procedures. For example, radiolabelled antibodies to specific tumor antigens are given to patients and the tumors are subsequently detected and localized by scintillation scanning. If desired, similar technology can be used to monitor the path and destination of the peptidyl inhibitors administered during the immunotherapy. Alternative methods exist for preparation of injectable compositions of peptidyl inhibitors and for administration of effective dosages to patients. Where alternative methods exist, the procedures used in the specific embodiments of this invention may be substituted by those skilled in the art.

It is also contemplated by this invention that cancer patients may obtain treatment with peptidyl inhibitors during ex vivo passage of body fluids. It is often inappropriate to administer parenterally a required drug, such as peptidyl inhibitors, for example, when a patient is already on a different drug therapy or a patient is intolerant or hypersensitive to the required drug. In such cases, ex vivo delivery of the required drug is the preferred method of treatment. In a specific embodiment of the invention, a body fluid, e.q., blood, lymph, cerebrospinal fluid, etc., is treated with a required peptidyl inhibitor, e.g., peptidyl diazomethyl ketone or peptidyl sulfonium salt outside the body. The ex vivo passage of body fluid is directed to flow through a medium (e.g., a solid support to which peptidyl inhibitors are attached) comprising an effective concentration of peptidyl inhibitor before being returned to the patient. Upon contact with the body fluid, the peptidyl inhibitor binds CP which is in the body fluid as a result of the presence of malignant cells therein. This contacting procedure may be repeated until essentially all free CP is bound and inactivated by peptidyl inhibitor before the body fluid is returned to the patient. Alternative methods exist for the preparation of chromatographic media containing peptidyl inhibitors and for the dialysis and filtration of body fluids. Where alternate methods are applicable for patient therapy, the ex vivo procedures used in the specific embodiments of this invention may be substituted by those skilled in the art.

It is further contemplated by the present invention to utilize the peptidyl diazomethyl ketone and peptidyl sulfonium salt reagents to rid blood of the presence of CP. In a preferred embodiment, freshly drawn blood or blood stored for later use is treated with a peptidyl inhibitor as a preventive measure against the presence of malignant cells. Since peptidyl inhibitors cause the destruction of malignant cells, exposure of a blood sample to an effective concentration of a peptidyl diazomethyl ketone or a peptidyl sulfonium salt destroys resident malignant cells. Such detoxified blood can be used, for example, for blood transfusions and other blood requirements that are medically and commercially mandated, without fear of the presence of malignant, potentially metastatic, cells.

The present invention will be further illustrated by the following examples. The examples are provided to aid in the understanding of the invention and are not to be construed as a limitation on the scope of the claimed invention.

EXAMPLE 1

Synthesis of Peptidyl Inhibitors (a) Synthesis of Z-Phe-Ala diazomethyl ketone

The blocked dipeptide, N-carbobenzyloxy-phenylalanylalanine (Z-Phe-Ala) was purchased from Sigma Chemical Co. (St. Louis, MO). The diazomethyl ketone derivative was synthesized by the mixed anhydride method of Green and Shaw (1981) J. Biol. Chem. 256:1923-1928). The blocked dipeptide was dissolved in dry tetrahydrofuran at −20° C. with isobutylchloroformate with N-ethylmorpholine for 15 min; the reaction mixture was then added to ethereal diazomethane (60 ml) at 0° C. After 30 min at 0° C., it was allowed to warm up overnight. The reaction mixture was washed with water, aqueous sodium bicarbonate, then dried over anhydrous magnesium sulfate. The residual material appeared to be pure by thin layer chromatography in methylene chloride:ethanol (10:1). Occasionally, the product crystallized out and, if necessary, was recrystallized or chromatographed on silica gel (Watanabe et al. (1979) supra) to obtain a homogenous product.

Prior to use, 20 mM stock solutions in 50% DMSO (dimethylsulfoxide) were prepared and diluted with 20 mM veronal buffer, pH 7.2, to provide working solutions such that the final organic solvent was 1% (v/v) or less. Dilutions of inhibitor were favored that gave relatively slow inactivations to avoid saturation effects and to permit the assay of 4–10 aliquots.

(b) Synthesis of Z-Phe-Gly diazomethyl ketone

Synthesis was performed essentially as described in example (a) except that the starting blocked dipeptide was N-carbobenzyloxy-phenylalanylglycine (Z-Phe-Gly).

(c) Synthesis of Z-Pro-Gly diazomethyl ketone

Synthesis was performed essentially as described in example (a) except that the starting blocked amino acids was N-carbobenzyloxy-proline (Z-Pro) to which glycine was added by established methods (Wunseh et al. (1971), Hoppe-Seyler's Z. Physiol. Chem. 352:1568–1579).

(d) Synthesis of Z-Gly-Gly-Val diazomethyl ketone

Synthesis was performed essentially as described in example (a) except that the starting blocked tripeptide was N-carbobenzyloxy-glycylglycyl valine (Z-Gly-Gly-Val).

(e) Synthesis of Z-Ala-Ala-Pro diazomethyl ketone

Synthesis was performed essentially as described in example (a) except that the starting blocked dipeptide was N-carbobenzyloxy-alanylalanine (Z-Ala-Ala) to which proline was added by established methods (Wunseh et al. (1971) supra).

(f) Synthesis of Z-Ala-Ala diazomethyl ketone

Synthesis was performed essentially as described in example (a) except that the starting blocked dipeptide was N-carbobenzyloxy-alanylalanine (Z-Ala-Ala).

(g) Synthesis of Z-Phe-Ala sulfonium salts

Z-Phe-Ala-CH$_2$-S$^+$(CH$_3$)$_2$ bromide and tetrafluoroborate salts were synthesized according to Shaw (1988) supra. A solution of Z-Phe-Ala-CH$_2$Br (300 mg) in benzene at about 50° C. was treated with dimethyl sulfide and allowed to cool. Solid began to separate after a few minutes. After 3 h, the product was filtered, washed liberally with benzene and dried. The sulfonium walt was recrystallized from alcohol and ether.

For conversion to the tetrafluoroborate salt, the sulfonium bromide (300 mg) in chloroform (15 ml) was stirred at 0° C. with saturated aqueous potassium carbonate (2 ml). After 10 min, the organic phase and washings were stirred with solid potassium carbonate and the filtrate taken to dryness. The residual oily ylide was taken up in absolute ethanol containing 50% aqueous HBF$_4$ (0.1 ml) and the solution taken to dryness. The evaporation, with added absolute ethanol, was repeated for completion of dehydration, leaving a crystalline residue. The fluoroborate salt was recrystallized from ethanol and ether.

Prior to use, the sulfonium salts were dissolved in 20% aqueous ethanol. They were diluted to a concentration of 20 mM in veronal buffer, pH 7.2, to prepare the stock solution; these stock solutions of each inhibitor were used for preparing the working solutions.

(h) Synthesis of Z-Phe-Lys sulfonium bromide

Z-Phe-Lys-CH$_2$-S$^+$(CH$_3$)$_2$ bromide was synthesized according to the method of Rauber et al. (1988) supra. Z-Phe-hydroxy-succinimide ester, N-methylmorpholine and H-Lys(-Boc)-OH were stirred in dimethylformamide at room temperature for 22 h. The filtrate was concentrated under reduced pressure to a syrup, which was taken up in ethyl acetate, extracted with aqueous 10% (w/v) citric acid then water, and dried with anhydrous MgSO$_4$. The residue was crystallized from ethylacetate/hexane.

Conversion to the tetrafluoroborate salt was performed as described in example (g).

EXAMPLE 2

Preparation of CP

Purified CP was prepared according to published methods (Falanga et al. (1985) Biochem. 24:5558–5567; Gordon et al. (1981) J. Clin. Invest. 67:1665–1671). Briefly, rabbit V2 carcinoma tumor tissue was extracted in veronal buffer, the extract was concentrated and applied to an immunoaffinity column (goat anti CP antibody coupled to Sepharose) and eluted with various concentration of urea in veronal buffer (20 mM, pH 7.2). The eluted fractions were applied to a PCMB affinity column and eluted with different concentrations of glutathione in veronal buffer. The characteristic properties of CP in all the samples were determined by analyzing procoagulant activity in citrated normal and factor VII deficient human plasma, by demonstrating inhibition by mercury and iodoacetamide and by verifying the 68 kd molecular weight by SDS-polyacrylamide gel analysis.

EXAMPLE 3

Assay for Procoagulant Activity (a) Activation of Factor X

The procoagulant activity of the samples and the controls was measured in a one-stage plasma recalcification clotting time assay using a model 202A clot timer (Heller Laboratories, Santa Rose, CA). The sample (0.1 ml) was added to 0.1 ml of citrated plasma prepared as described by Gordon et al. (1981) supra, and prewarmed for min at 37° C. The reaction was started by adding 0.1 ml of prewarmed 25 mM CaCl$_2$. If the volume of the sample was too small, 0.05 ml of the sample was used with proportional reduction in the volume of the other reagents. An RVV (Russell's viper venom) standard curve was prepared from $10^{-1}$ to $10^{-6}$ dilution of stock, commercial RVV (Sigma Chemical Co., St. Louis, MO), according to the specification in the technical bulletin. These dilutions of RVV were used to calibrate the assay plasma and to verify linearity of the clotting times over the range of procoagulant activity.

The procoagulant activity of the samples was expressed as clotting time in seconds or as the percent activity, calculated as the percent reduction of clotting time (CT) from the corresponding buffer blank [(blank time (sec)−sample clotting time (sec))/ blank time (sec)]×100. The percent inhibition of the control and experimental procoagulants by the peptidyl diazomethyl ketone and peptidyl sulfonium salt inhibitors was expressed as the percent increase in the clotting time compared with the uninhibited sample [(inhibited CT−uninhibited CT)/uninhibited CT]×100.

(b) Inactivation of Protein C System (i) Effect of CP on Thrombomodulin

Thrombomodulin (TM) functions in the activation of protein C. Protein C was purified from human placenta according to the method of Kisiel (1979) J. Clin. Invest. 64:761-769, and recombinant protein C was obtained as a gift from Integrated Genetics, Boston, MA. Human placental TM was purified according to the method of Salem et al. (1984) J. Biol. Chem. 259:12246-12251. In the presence of TM, thrombin and calcium ions, human protein C, or recombinant protein C, was rapidly converted to its activated form. Formation of activated protein C was monitored according to the method of Marlar et al. (1988) Fibrinolysis 2 (Suppl. 1):154.

TM was shown to be sensitive to inactivation by cancer procoagulant (CP). Purified CP enzyme was incubated with purified soluble human TM for various lengths of time up to 120 minutes in the presence and absence of calcium ions. In the presence of calcium ions, CP rapidly inactivated TM in a time dependent fashion. Approximately 65% of the starting TM activity was destroyed within 60 minutes. In the absence of calcium ions, only 15% was destroyed during the 60 minute incubation. Based on these results, TM is inactivated by CP in a time dependent fashion which required calcium ions for optimal function. The amount and rate of inactivation suggests that CP may physiologically regulate the thrombin-TM reaction in vivo.

To determine whether the time-dependent loss of activity is enzymatic inactivation of TM by CP or stoichiometric binding of the CP molecule to TM, studies on the dose-dependent interaction of CP and TM were performed. The activity of 100 nM TM was incubated with from 0 to 1.5 nM of purified CP for 60 minutes at 37° C. and the level of TM inactivation was measured, The enzyme (CP) to substrate (TM) ratio varied from 1:67 (at 1.5 nM CP) to 1:533 (at 0.188 nM CP). The results indicated that TM inactivation is an enzymatic reaction. Other preliminary studies of the interaction of the CP enzyme and the protein C system produced no evidence that thrombin and CP competed for TM binding and showed that CP neither activated nor inactivated purified protein C.

(ii) Effect of CP on Protein S

Protein S has been purified from human plasma by both conventional purification techniques and immunoaffinity chromatography (Fair et al. (1986) Blood 67:64-70; Blood 67:1168-1171; Szatkowski et al. (1984) Circulation 70:204-206). To determine the role of CP in the regulation of protein S, purified protein S was incubated with highly purified CP in the presence of calcium ions. An aliquot of the reaction mixture was removed at various times and added to sodium dodecyl sulfate (SDS). The samples were run on SDS-PAGE and Western blotted with polyclonal anti-protein S antisera (produced using conventional methods). Within 10 minutes, two new forms of protein S were observed. The first form, having an approximate molecular weight of 65 kD, appeared rapidly and remained in fairly consistent amount throughout the 60 minute time course of the study. The second band, having an approximate molecular weight of 55 kD, appeared more slowly and accumulated with time. Calcium ions were required to show the appearance of the protein S degradation bands

EXAMPLE 4

Inhibition Studies (a) Method for Measuring Inhibition

Papain, a factor X activator and cysteine proteinase standard, RVV (Russell's viper venom) and rabbit brain thromboplastin, a tissue factor (TF) standard, were purchased from Sigma Chemical Co. (St. Louis, MO). To determine the effect of the peptidyl diazomethyl ketone and peptidyl sulfonium salt inhibitors on CP, the control procoagulants (Papain, RVV and TF), and the assay plasma system, the procoagulant activity of the samples and controls was analyzed with and without the addition of different concentrations of the inhibitors. In each case, blank samples were prepared by diluting either 50% DMSO or aqueous ethanol (the solvents for the peptidyl inhibitors) into the appropriate volume of buffer; there was no effect of these solvents on the assay plasma activity. Preliminary experiments evaluated the time (15, 30 and 50 min) and temperature (25° C. and 37° C.) of the inhibition reaction; 30 min at 25° C. was selected as the optimum conditions and was used for the subsequent studies. Peptidyl diazomethyl ketone inhibitors were incubated with the procoagulant samples at a final concentration of 400 $\mu$M, 200 $\mu$M, 100 $\mu$M, 10 $\mu$M and 1 $\mu$M. Peptidyl sulfonium salt inhibitors were incubated with the samples at a final concentration of 800 $\mu$M, as well as the same concentrations as the diazomethyl ketones. At the end of the inhibition incubation, each sample was analyzed in the coagulation assay.

An unpaired student t test was used to analyze the difference between % inhibition of papain and CP by the different PDK and PSS inhibitors.

Each CP or control sample was adjusted to a concentration such that the procoagulant activity reduced the clotting time of the blank assay plasma from 10% to 30%, within the linear range of the assay (Gordon et al. (1979) J. Natl. Cancer Inst. 62:773-776). Furthermore, control samples were always adjusted to a clotting time comparable to the CP sample so that demonstrated inhibition of CP was compared to similar inhibition of the controls.

(b) Effect of Peptidyl Inhibitors on Control Samples

Figure 1:
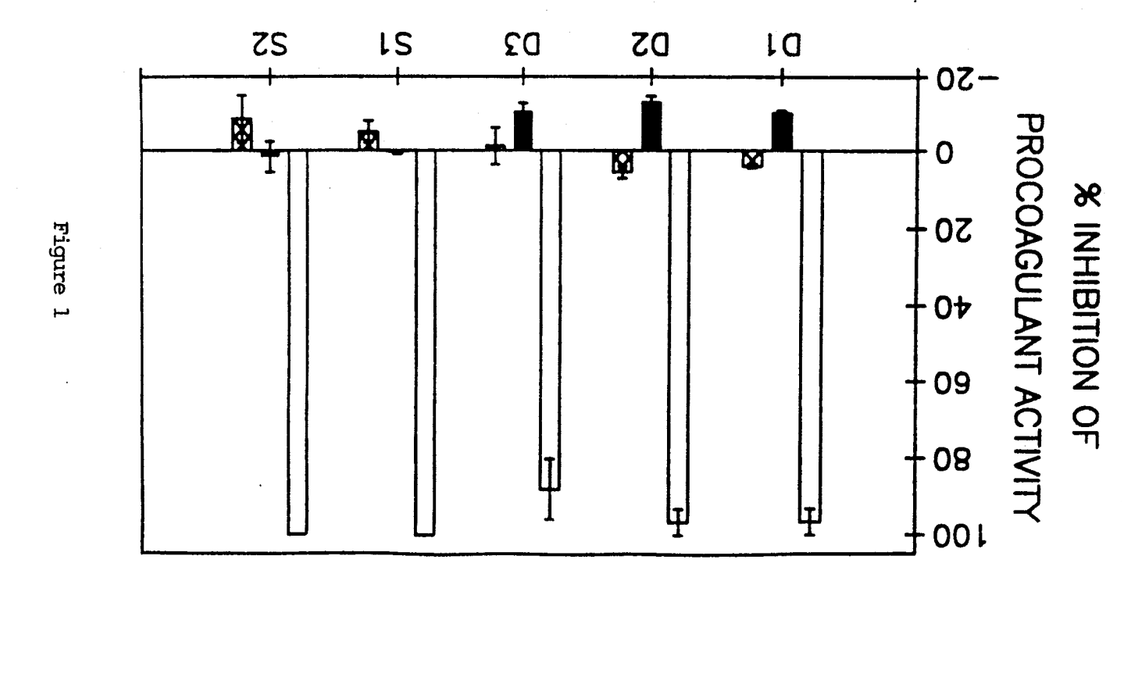
FIG. 1 documents the extent of inhibition of assay controls by 200 μM peptidyl diazomethyl ketones and by 400 μM peptidyl sulfonium salts. Samples of papain (☐), RVV (■) and TF (■) were incubated for 30 minutes at 25° C. with either Z-Phe-Ala diazomethyl ketone (D1), Z-Phe-Gly diazomethyl ketone (D2), Z-Pro-Gly diazomethyl ketone (D3), Z-Phe-Ala-$CH_2S^+(CH_3)_2$ (S1) or Z-Phe-Lys-$CH_2S^+(CH_3)_2$ (S2). Procoagulant activity was assayed by measuring the recalcification clotting time of normal citrated plasma. Papain was inhibited. Neither RVV, TF nor the assay plasma was inhibited by either the peptidyl diazomethyl ketones or peptidyl sulfonium salts.

The effect of the inhibitors was tested on the control procoagulants (TF, RVV and Papain) to determine if they affected the procoagulants or the assay plasma. FIG. 1 shows the effect of 200 $\mu$M of Z-Phe-Ala diazomethyl ketone (D1), Z-Phe-Gly diazomethyl ketone (D2) and Z-Pro-Gly diazomethyl ketone (D3), and 400 $\mu$M Z-Phe-Ala sulfonium bromide (S1) and Z-Phe-Lys sulfonium bromide (S2) on papain, RVV and TF. There was 97% inhibition of papain by D1 and D2, 88% inhibition by D3 and 100% inhibition by S1 and S2. In contrast, RVV showed slight activation, resulting in a negative percent inhibition of from −10% to −13%, by each of the peptidyl diazomethyl ketones. TF showed no significant inhibition. Neither S1 nor S2 affected the activity of RVV and TF activity was slightly enhanced by both S1 (5%) and S2 (8%), resulting in a negative inhibition. Thus, neither the assay plasma nor RVV and TF, the control procoagulants that function via serine proteinase activity, were affected by either the peptidyl diazomethyl ketone or peptidyl sulfonium salt reagents, while the cysteine proteinase control procoagulant was slightly inhibited. The effect of Z-Gly-Gly-Val diazomethyl ketone (D4), Z-Ala-Ala-Pro diazomethyl ketone (D5) and Z-Ala-Ala diazomethyl ketone (D6) on the coagulation controls and the assay plasma gave essentially the same results.

(c) Differential Effect of Peptidyl Inhibitors on Cysteine Proteinases

Comparison of the inhibition of papain and CP at 100 $\mu$M peptidyl diazomethyl ketone was done to determine whether or not each compound affected cysteine activity to the same extent. FIG. 2 shows that D1 (Z-Phe-Ala diazomethyl ketone) and D2 (Z-Phe-Gly) were about equally effective in blocking the activity of papain (85% and 88% inhibition, respectively). Inhibition of CP was somewhat less by D1 (68%) than by D2 (97%). There was no difference between the inhibition of papain and CP by D1 but D2 was significantly more effective at blocking CP than papain (p>0.01). D3 (Z-Pro-Gly diazomethyl ketone) was a much less effective inhibitor of both CP (31%) and papain (15%) than D1 (p>0.05) or D2 (p>0.01). D4 (Z-Gly-Gly-Val diazomethyl ketone) and D5 (Z-Ala-Ala-Pro diazomethyl ketone) had little effect (2% inhibition) on the activity of papain while they were significantly more effective inhibitors of CP (p>0.05), about 48% and 62% inhibition, respectively. D6 (Z-Ala-Ala diazomethyl ketone) inhibited the activity of CP (92%) more than the activity of papain (31%) (p>0.01). Thus, there was dramatically different inhibition demonstrated by the different peptidyl diazomethyl ketones on both of the cysteine proteinases.

The effect of different concentrations of peptidyl sulfonium salt inhibitors was measured (FIG. 3). Papain was completely inhibited at 400 $\mu$M, 200 $\mu$M, and 100 $\mu$M S1 (Z-He-Ala-CH$_2$S$^+$(CH$_3$)$_2$Br); S2 (Z-Phe-Lys-CH$_2$S$^+$(CH$_3$)$_2$Br) had almost the same effect. At 10 $\mu$M, the activity of papain was inhibited 55% by S1 and 20% by S2. In contrast, both sulfonium salts were less effective inhibitors of CP; the activity of CP was inhibited 62% by 400 $\mu$M S1 and 72% by S2. S1 and S2, at 200 $\mu$M, inhibited CP 51% and 54%, respectively. There was 26% and 33% inhibition of CP by S1 and S2 at 100 $\mu$M and there was no inhibition of CP at 10 $\mu$M of the peptidyl sulfonium salts.

EXAMPLE 5

Cytotoxicity of Peptidyl Inhibitors

Peptidyl diazomethyl ketones and peptidyl sulfonium salts that inhibit CP are prepared as described in Example 1. Each peptidyl inhibitor is mixed with 50,000 B16-F10 mouse melanoma cells and incubated for 30 minutes at 25° C. The cells are examined by phase contrast microscopy and appear to be lysed. To check for viability, cells are replated back in tissue culture medium under the standard growing conditions for the B16 melanoma cells and no cells grow out of the replating experiment. These results show that the peptidyl inhibitors of CP have a direct effect on cell viability of tumor cells.

EXAMPLE 6

Treatment with Peptidyl Inhibitor to Reduce Metastatic Capacity of Malignant Cells Forty Balb/C mice are arbitrarily divided into four groups of ten mice each as schematically illustrated in Table Group I is pretreated with an injectable composition devoid of peptidyl inhibitor (no inhibitor control). Group II is pretreated with an injectable composition containing peptidyl inhibitor. An injectable composition is prepared in a sterile solution comprising per ml: (a) 10 mg bovine serum albumin, (b) 0.01M phosphate buffer, pH 7.5, (c) 0.9% NaCl, (d) 0.01–50.0 mg peptidyl inhibitor prepared as discussed in Example 1, solubilized in either 50% DMSO or ethanol and diluted with 20mM veronal buffer, pH 7.2, such that the final organic solvent is 1% or less. The inhibitor control contains all components except the inhibitor compound; however, appropriate amounts of DMSO, ethanol and veronal buffer are included in the control. Pretreatment with either control or peptidyl inhibitor is followed by an incubation period of 15 to 60 minutes.

TABLE 1

| Treatment Sequence | Design of Experiment Group | | | |
|---|---|---|---|---|
| | I | II | III | IV |
| Pretreatment w/control | + | | | |
| Pretreatment w/inhibitor incubate 15–60 minutes | | + | | |
| Melanoma cell injection incubate 15 days | + | + | + | + |
| Treatment w/control | | | + | |
| Treatment w/inhibitor incubate 15 days sacrifice | | | | + |

B16-F10 variants of the mouse melanoma cells are grown in tissue culture as described by Gordon et al. (1982) Thromb. Res. 26:379–387. Briefly, cells are grown in early passage, harvested and cell suspension are prepared for injection into the mice. Fifty-thousand cells per 0.1 ml of serum-free tissue culture medium are prepared and injected into the tail vein of each mouse according to the procedures described by Gilbert et al. (1983) Cancer Res. 43:536–540. Fifteen days after inoculation of the B16 melanoma cells, Group III is treated with an injectable composition devoid of peptidyl inhibitor (no inhibitor control), while Group IV is treated with an injectable composition containing peptidyl inhibitor. Thirty days after inoculation of the B16 melanoma cells, the mice are sacrificed and the number of lung colonies are counted. The control mice (Groups I and III) contain from 25 to 35 lung colonies per mouse, the peptidyl inhibitor pretreated mice (Group II) contain from zero to three lung colonies per mouse, and the mice obtaining post-treatment with peptidyl inhibitors (Group IV) have from one to ten lung colonies per mouse. Not only is there a significant reduction in metastatic capacity of B16 cells in peptidyl inhibitor-treated animals (compare Groups I and II), but also there is an apparent reduction/destruction of established colonies (compare Groups III and IV). As is known in the art, alternate methods exist to test metastatic capacity of primary tumors. Hence it is contemplated that modifications of the specified method will be encompassed by the instant invention. Moreover, the animal model used in the specific embodiments of this invention may be substituted by those skilled in the art.

EXAMPLE 7

Treatment with Peptidyl Inhibitors to Reduce Metastatic Capacity of Primary Tumors In this example, a primary tumor is allowed to metastasize spontaneously to a secondary site. The protocol is schematically illustrated in Table 2. Essentially the same pretreatment protocol is followed as that described in Example 6. Group I represents a no inhibitor control group, while Group II is pretreated with peptidyl inhibitor; pretreatment is maintained for 15-60 minutes.

TABLE 2

| Treatment Sequence | Experimental Design Group | | | |
|---|---|---|---|---|
| | I | II | III | IV |
| Pretreatment with control | + | | | |
| Pretreatment with inhibitor | | + | | |
| incubate 15-60 minutes | | | | |
| Melanoma cell injection | + | + | + | + |
| incubate 21 days | | | | |
| amputate | | | | |
| incubate 4 weeks | | | | |
| Treatment with control | | | + | |
| Treatment with inhibitor | | | | + |
| incubate 4 weeks | | | | |
| sacrifice | | | | |

B16-F10 variants of B16 melanoma are grown in tissue culture and a cell suspension is prepared in serum-free medium. A suspension of 50,000 cells is injected into the footpad of the mice in all groups and tumors are allowed to grow for 21 days. At three weeks, the foot is amputated such that the primary tumor is removed and the mice are maintained for four weeks. At that time Group III is treated with an injectable composition devoid of peptidyl inhibitor (no inhibitor control) while Group IV is injected with peptidyl inhibitor. Alternatively, this step may be changed so that peptidyl inhibitor or control is given one day prior to amputation. The mice are then maintained for an additional four weeks at which time they are sacrificed and lung colonies are counted. More preferably, during the four weeks of incubation, booster amounts of inhibitor or inhibitor control are administered at given intervals. The results show that approximately 80% of the control animals (Groups I and III) have metastatic tumors, whereas only about 20% of the peptidyl inhibitor pretreated mice (Group II) and approximately 45% of the mice post-treated with peptidyl inhibitor (Group IV) have metastatic tumors. This reduction in metastatic capacity of primary tumors confirms the data on metastatic capacity of malignant cells documented in Example 6. As is known in the art, the animal model used in the specific embodiments of this invention may be modified or substituted by those skilled in the art.

EXAMPLE 8

Cancer Therapy with Peptidyl Inhibitors (a) Administration of Peptidyl Inhibitors to Cancer Patients Intravenous injection of a peptidyl diazomethyl ketone or peptidyl sulfonium salt (synthesized according to the procedures described in Example 1) is given to a cancer patient for the immediate purpose of decreasing existing tumor size and to reduce tumor metastasis. It may also be used as adjuvant therapy in conjunction with, for example, chemical or radiation therapy; or as a preventive measure in cancer patients before or during surgery when the incidence of tumor perturbation leading to malignant cell shedding and metastasis may occur with increased probability.

A patient having cancerous growth, ascertained by usual methods of tumor detection, is injected by intravenous infusion of 50-100 ml of sterile physiological saline containing 0.01-50.0 mg of peptidyl inhibitor of CP per kg weight of patient and delivered over a period of 15-60 min. Patients are pretested for anaphylactic hypersensitivity to the foreign, chemically synthesized peptidyl inhibitors. Dose levels of peptidyl diazomethyl ketones and peptidyl sulfonium salts ranging from 1 to 60 mg per kg body weight are tolerated in humans. After intravenous therapy, tumor size and extent of metastasis are monitored at regular intervals. The dose is repeated as necessary at intervals adjusted on an individual basis.

Peptidyl diazomethyl ketone and peptidyl sulfonium salt inhibitors can also be injected directly into tumors. The precise localization of a tumor is carried out using established medical diagnostic procedures. For example, radiolabelled antibodies to specific tumor antigens are given to patients and the tumors are subsequently detected and localized by scintillation scanning (Hansen, U.S. Pat. No. 3,927,193; Goldberg, U.S. Pat. Nos. 4,331,647, 4,348,376 and 4,361,544).

An injectable composition of peptidyl inhibitor is prepared in a sterile solution comprising per ml:

(a) 10 mg human serum albumin
(b) 0.01 M phosphate buffer, pH 7.5
(c) 0.9% NaCl
(d) 0.01-50.0 mg peptidyl diazomethyl ketone or peptidyl sulfonium salt prepared as discussed above in Example 1.

From 1 to 10 ml of injectable composition of anti-human CP globulins is injected into predefined tumor locations. The tumor size is monitored at regular intervals. Injections are repeated as necessary at intervals adjusted on an individual basis.

(b) Contacting Body Fluids with Peptidyl Inhibitors

It is often undesirable to administer parenterally a needed drug to a cancer patient if, for example, that patient is already on a different drug therapy or that patient is intolerant or hypersensitive to the required drug. In such cases, ex vivo administration of a required drug is the highly preferred method of treatment.

In patients diagnosed as having a tumor, treatment with a CP inhibitor, for example, peptidyl diazomethyl ketone or peptidyl sulfonium salt (synthesized according to the procedures of Example 1), is advocated to decrease tumor size and to reduce or prevent tumor metastasis. A body fluid, e.g., blood, lymph, cerebrospinal fluid, etc., is treated with the required peptidyl inhibitor outside the body. The ex vivo passage of body fluid is directed to flow through a medium (e.g., a solid support to which peptidyl inhibitors are attached) comprising an effective concentration of peptidyl inhibitor before being returned to the patient. Contacting the body fluid with peptidyl inhibitor promotes binding of CP to the inhibitor; this contacting procedure may be repeated until essentially all CP is bound with peptidyl inhibitor before the body fluid is returned to the patient.

Tumor size is monitored at regular intervals. Ex vivo treatment with peptidyl inhibitors is repeated as necessary at intervals adjusted on an individual basis.

(c) CP Removal from Blood Using Peptidyl Inhibitors

Freshly drawn blood or blood stored for later use can be treated with peptidyl inhibitors (synthesized according to the procedures described in Example 1) as a precaution against the presence of malignant cells. Since peptidyl inhibitors are cytotoxic and kill malignant cells, exposure of a blood sample to an effective concentration of a peptidyl diazomethyl ketone or a peptidyl sulfonium salt destroys resident malignant cells. Damaged cell debris and any unbound peptidyl inhibitor molecules are removed from the blood sample by methods routinely used in the art. Such detoxified blood, freed of malignant cells and foreign peptidyl inhibitor substances, can be used, for example, for blood transfusions, without fear of the presence of metastatic cancer cells.

EXAMPLE 9

The Site of Activation of Human Factor X by CP (a) Materials and Methods

Veronal buffer, bis-tris propane buffer, rabbit brain cephalin, $CaCl_2$ and Guanidine-HCl were purchased from Sigma Chemical Co. (St. Louis, MO). Precast Tris-Tricine SDS-PAGE gels were purchased from Novex (Encinitas, CA 92024). The ProBlott PVDF-type membrane was purchased from Applied Biosystems and the 3-cyclohexylamino-1-propane sulfonic acid (CAPS) buffer was purchased from Aldrich Chem. Co. (Milwaukee, WI). Purified human factor X and human factor Xa were purchased from Hematologic Technologies (Essex Junction VT).

Fresh human placenta was obtained from the delivery deck, the amnion-chorion membranes were removed from the placental tissue and extracted in 3 to 4 changes of 20 mM veronal buffer (pH 7.4) as described in Gordon et al. (1985) Blood 66:1261-1265. The extracts were purified over an anti-Cp antibody affinity column. The purified CP sample was assayed for procoagulant activity by measuring clotting time of normal and factor VII deficient citrated plasma. The inhibition of the activity by 1 mM iodoacetamide in water and 0.1 mM $HgCl_2$ in water was used to verify its cysteine proteinase characteristics. To assure that there was no tissue factor-factor VIIa activity in the preparation, 5 μl (1.3 mg/ml) of rabbit polyclonal anti-tissue factor antibody was added to the sample and incubated for 30 min. at 25° C. There was no evidence of activity in factor VII deficient plasma and all the procoagulant activity was inhibited by iodacetamide and $Hg^{++}$.

To determine the cleavage site of factor X, a reaction mixture containing purified CP (0.5 to 8 μg) in 100 μl of 20 mM bis-tris propane buffer (pH 6.5), 8 μl of 1 mg/ml of crude rabbit brain phospholipid and 5 μl of anti-tissue factor antibody was incubated for 30 min. at 25° C. 20 μl were removed to assay CP activity. The sample was diluted to 400 μl with bis-tris buffer and assayed in factor VII deficient plasma to verify the level of activity. To initiate the reaction in the remainder of the sample, 25 to 30 μg of purified human factor X and 8 μl of $CaCl_2$ were added a 10 μl sample was immediately removed as the zero time sample, 10 μl of SDS-PAGE sample buffer was added and it was heated to 70° C. for 10 min. and saved. The remainder of the mixture was incubated at 37° C. for 12 hours. At the end of the incubation, the sample was dried in a vacuum centrifuge, redissolved in 15 μl of water, an equal volume of SDS-PAGE sample buffer was added and the mixture was heated to 70° C. for 10 min.

The zero time sample, a sample of purified human factor Xa standard, molecular weight standards and 4 consecutive wells of the 12 hour reaction mixture were electrophoresed on a Tris-tricine gel. The proteins were electroeluted onto a ProBlott PVDF membrane and the membrane and the electroeluted tricine gel were stained Coomassive Blue to visualize the proteins. There were no proteins remaining on the tricine gel. The factor Xa protein band on the membrane was identified, carefully cut from the rest of the membrane and the pieces of membrane containing the factor Xa protein were placed in the sample chamber of an Applied Bio-system 477A microsequencer with on line HPLC. Up to 8 residues of the amino acid sequence of the factor Xa peptide was determined. The experiment was repeated 4 times, with 3 different samples of purified CP.

(b) Site of Cleavage by CP

Figure 4:
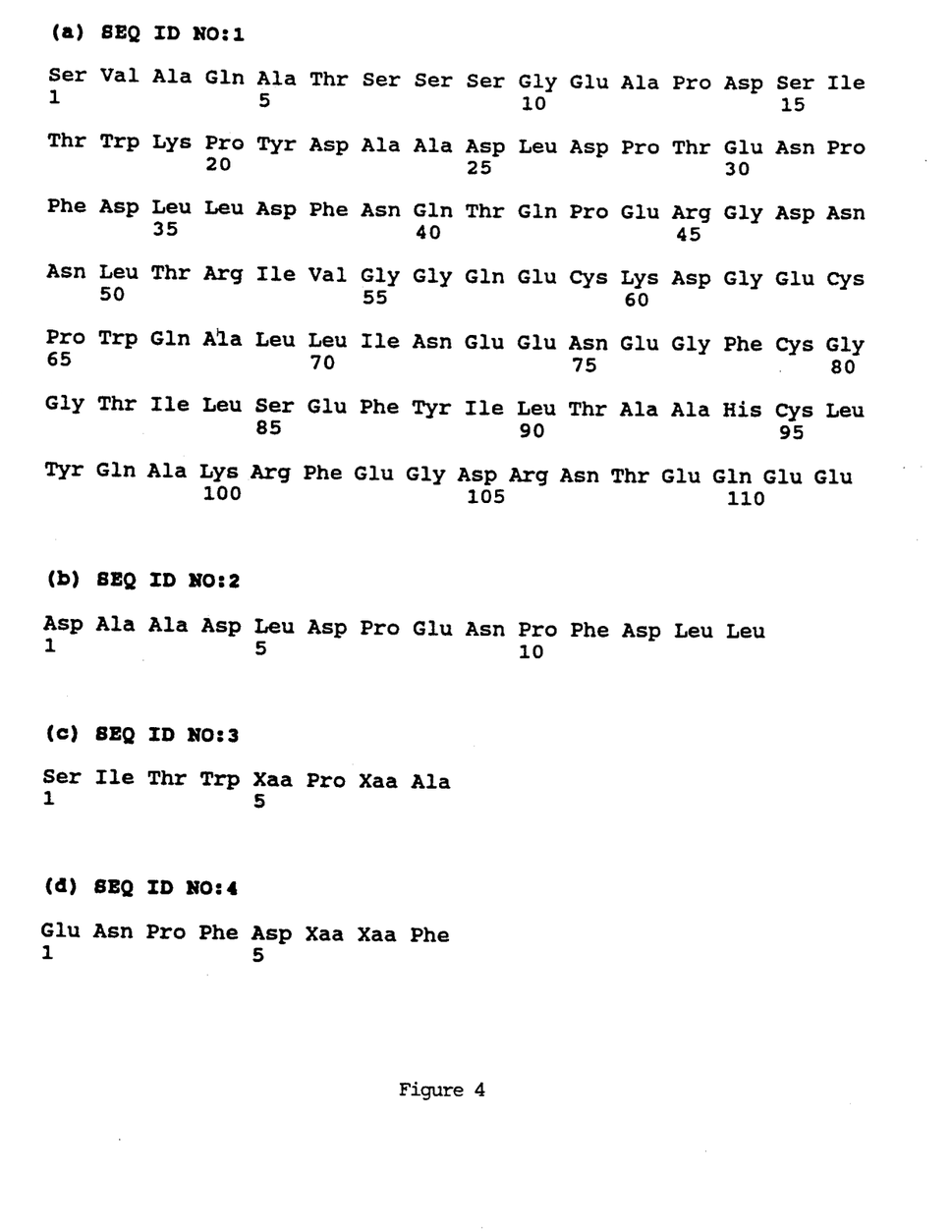
FIG. 4 documents (a) the partial, N-terminal amino acid sequence of Factor $X_a$ heavy chain as per Leytus et al. (1984) Proc. Natl. Acad. Sci. USA 81:3699–3702 (SEQ ID NO:1) and of three peptides [(b) SEQ ID NO:2, (c) SEQ ID NO:3 and (d) SEQ ID NO:4] produced upon interaction of Factor X with cancer procoagulant.

The activity of the purified CP sample at time zero was between 10% and 25% reduction in clotting time. The amino acid sequences for the 4 experiments are shown in FIG. 4. In one study, there were 2 sequences in the heavy chain of activation peptide, one was the Ser-Ile-Thr- sequence (SEQ ID NO:3), and the other was the Glu-Asn-Pro- sequence (SEQ ID NO:4). It was the only time that these sequences appeared. The more reproducible sequence, that was found the in the other 3 experiments, was the Asp-Ala-Ala-Asp- sequence (SEQ ID NO:2). The prior art teaches that cysteine proteinases are governed by the P2 amino acid on the carboxyl side of the hydroxylzed bond. Thus, it is indicated that the primary cleavage site of factor X is governed by proline-20 and the secondary sites are governed by proline-13 and -28.

The cysteine proteinase nature of CP would lead one to suspect that it might have different specificity than the serine proteinases that normally activate factor X. However, there is no evidence that factor X can be activated by cleavage of other amino acid bonds. Papain is known to activate factor X but there have been no studies to determine the site of activation. Since papain seeks a phenylalanine in the P2 position, it is very unlikely that it activates at arginine-52, like RVV and factors IXa and VIIa. There are no other known cysteine proteinases that activate factor X.

We claim:

1. A method of inhibition of cancer procoagulant with a selective peptidyl inhibitor of cancer procoagulant wherein said peptidyl inhibitor has the formula wherein Z is a substituent selected from the group consisting of H, alkyl, phenyl, benzyl, carbobenzyloxy, t-butoxy carbonyl, tosyl and 7-amino-4-methyl-coumaryl, R is an amino acid side chain or a modified or derivatized amino acid side chain selected independently from the group consisting of L-amino acids such that the peptide comprises amino acid residues that are the same or different from each other but wherein the penultimate amino acid residue is not phenylalanine, n is two or three, and Y is a substituent selected from the group consisting of OH, diazomethyl, (—CHN$_2$) and methylsulfonium group, where X$_1$ and X$_2$ are alkyl, phenyl, or benzyl groups and wherein said peptidyl inhibitor shows at least approximately 10-fold higher relative inhibitory activity to cancer procoagulant than to a cysteine proteinase other than cancer procoagulant.

2. The method of inhibition of cancer procoagulant of claim 1 wherein said peptidyl inhibitor shows at least approximately 100-fold higher relative inhibitory activity to cancer procoagulant than to a cysteine proteinase other than cancer procoagulant.

3. The method of inhibition of cancer procoagulant of claim 1 wherein said inhibitor is a dipeptidyl compound having the formula wherein Z is carbobenzyloxy, Y is a diazomethyl or a methylsulfonium group, R$_1$ is a side chain of an amino acid selected from the group consisting of glycine, alanine, valine, leucine, isoleucine, phenylalanine, tryptophan, threonine, tyrosine, aspartate, glutamate, methionine and proline, and R$_2$ is an amino acid side chain which is not phenylalanine.

4. The method of inhibition of cancer procoagulant of claim 3 wherein said R$_1$ is selected from the group consisting of glycine and alanine.

5. The method of inhibition of cancer procoagulant of claim 3 wherein said R$_1$ and R$_2$ amino acid side chains are selected from the group consisting of glycine and alanine.

6. The method of inhibition of cancer procoagulant of claim 3 wherein R$_1$ is a side chain of an amino acid selected from the group consisting of tyrosine, phenylalanine and threonine and R$_2$ is proline.

7. The method of inhibition of cancer procoagulant of claim 1 wherein said inhibitor is a tripeptidyl compound having the formula wherein Z is carbobenzyloxy, Y is a diazomethyl or a methyl-sulfonium group, R$_1$ is a side chain of an amino acid selected from the group consisting of glycine, alanine, valine, leucine, isoleucine, phenylalanine, tryptophan, threonine, tyrosine, aspartate, glutamate, methionine and proline, and R$_2$ and R$_3$ are amino acid side chains but wherein R$_2$ is not phenylalanine.

8. The method of inhibition of cancer procoagulant of claim 7 wherein Y is a diazomethyl group, R$_1$ is a side chain of an amino acid selected from the group consisting of glycine, alanine, valine and proline.

9. The method of inhibition of cancer procoagulant of claim 8 wherein R$_2$ and R$_3$ are side chains of amino acid selected from the group consisting of glycine and alanine.

10. The method of inhibition of cancer procoagulant of claim 8 wherein R$_1$, R$_2$ and R$_3$ are side chains of amino acids selected from the group consisting of glycine and alanine.

11. The method of inhibition of cancer procoagulant of claim 7 wherein Y is a diazomethyl group, R$_1$ is the side chain of valine, R$_2$ is the side chain of glycine, and R$_3$ is the side chain of glycine.

12. The method of inhibition of cancer procoagulant of claim 7 wherein Y is a diazomethyl group, R$_1$ is the side chain of proline, R$_2$ is the side chain of alanine, and R$_3$ is the side chain of alanine.

13. The method of inhibition of cancer procoagulant of claim 7 wherein R$_1$ is a side chain of an amino acid selected from the group consisting of aspartate and glutamate and R$_2$ and R$_3$ are side chains of amino acids selected from the group consisting of glycine and alanine.

14. The method of inhibition of cancer procoagulant of claim 7 wherein R$_1$ is a side chain of an amino acid selected from the group consisting to tyrosine, phenylalanine and threonine, R$_2$ is the side chain of proline and R$_3$ is a side chain of an amino acid selected from the group consisting of alanine, lysine and aspartate.

15. The method of inhibition of cancer procoagulant of claim 14 wherein R$_3$ is the side chain of lysine.

* * * * *

UNITED STATES PATENT AND TRADEMARK OFFICE
CERTIFICATE OF CORRECTION

PATENT NO. : 5,223,486

DATED : June 29, 1993

INVENTOR(S) : Stuart G. Gordon; Anna Falanga

It is certified that error appears in the above-indentified patent and that said Letters Patent is hereby corrected as shown below:

At column 3, line 21, insert a colon after "76". At column 3, line 65, rewrite "$1.7-10^{-6}M$" as --$1.7 \times 10^{-6}M$--. At column 4, line 58, rewrite "$Z\text{-He-Ala-}CH_2S^+(CH_3)_2$" as --$Z\text{-Phe-Ala-}CH_2S^+(CH_3)_2$--. At column 5, line 13, rewrite "7575" as --757--. At column 5, line 18, rewrite "Z-Phe-Al a" as --Z-Phe-Ala--. At column 10, line 33, rewrite "CH-" as --$CH_2$--. At column 10, line 34, remove "$_2$" at the beginning of the line. At column 12, line 26, rewrite "Cp" as --CP--. At column 14, line 18, rewrite "e.q." as --e.g.--. At column 15, line 60, rewrite "walt" as --salt--. At column 16, line 58, insert --1-- before "min". At column 19, line 45, rewrite "$Z\text{-He-Ala-}CH_2S^+(CH_3)_2Br$" as --$Z\text{-Phe-Ala-}CH_2S^+(CH_3)_2Br$--. At column 20, line 9, insert --1.-- after "Table". At column 23, line 41, rewrite "Cp" as --CP--. At column 23, line 64, insert --and-- after "added". At column 24, line 36, rewrite "hydroxylzed" as --hydrolyzed--. In claim 7 rewrite the formula as:

Signed and Sealed this

Twenty-sixth Day of April, 1994

*Attest:*

BRUCE LEHMAN

*Attesting Officer*  Commissioner of Patents and Trademarks